US012802802B2

(12) United States Patent
Orasanu et al.

(10) Patent No.: US 12,802,802 B2
(45) Date of Patent: Nov. 17, 2026

(54) MESH TOPOLOGY ADAPTATION

(71) Applicant: KONINKLIJKE PHILIPS N.V., Eindhoven (NL)

(72) Inventors: Eliza Teodora Orasanu, Hamburg (DE); Fabian Wenzel, Hamburg (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 413 days.

(21) Appl. No.: 17/780,973

(22) PCT Filed: Dec. 10, 2020

(86) PCT No.: PCT/EP2020/085394

§ 371 (c)(1),
(2) Date: May 28, 2022

(87) PCT Pub. No.: WO2021/116238

PCT Pub. Date: Jun. 17, 2021

(65) Prior Publication Data

US 2022/0415481 A1 Dec. 29, 2022

(30) Foreign Application Priority Data

Dec. 12, 2019 (EP) .................................... 19215636

(51) Int. Cl.
*G16H 30/40* (2018.01)
*G06T 7/10* (2017.01)
*G06T 7/33* (2017.01)

(52) U.S. Cl.
CPC ............... *G16H 30/40* (2018.01); *G06T 7/10* (2017.01); *G06T 7/344* (2017.01)

(58) Field of Classification Search
CPC ........... G06T 7/10; G06T 7/344; G06T 19/20; G06T 2207/10028; G06T 2207/30016; G06T 7/168; G06T 7/12; G16H 30/40
USPC .......................................................... 382/100
See application file for complete search history.

(56) References Cited

U.S. PATENT DOCUMENTS

| | | | | |
|---|---|---|---|---|
| 11,216,945 | B2 | 1/2022 | Wang | |
| 2009/0213138 | A1* | 8/2009 | DeRose | G06T 17/20<br>345/619 |
| 2011/0295515 | A1* | 12/2011 | Grady | A61B 5/055<br>702/19 |

(Continued)

FOREIGN PATENT DOCUMENTS

| | | |
|---|---|---|
| EP | 3514757 A1 | 7/2019 |

OTHER PUBLICATIONS

Metric Optimization for Surface Analysis in the Laplace-Beltrami Embedding Space (Year: 2014).*

(Continued)

*Primary Examiner* — Jennifer Mehmood
*Assistant Examiner* — Pardis Sohraby

(57) ABSTRACT

Presented are concepts for adapting a first, pre-defined mesh topology representing an organ to a second, different mesh topology of the organ. One such concept includes identifying correspondence between the first and second mesh topologies based on spectral matching of the first and second mesh topologies. The first, predefined mesh topology is aligned with the second mesh topology based on the identified correspondence between the first and second mesh topologies.

18 Claims, 3 Drawing Sheets

(56) References Cited

U.S. PATENT DOCUMENTS

| | | | | |
|---|---|---|---|---|
| 2016/0078633 | A1* | 3/2016 | Tahmasebi Maraghoosh | G06T 7/174 382/131 |
| 2016/0379372 | A1* | 12/2016 | Groth | G06T 7/149 382/131 |
| 2020/0342603 | A1* | 10/2020 | Orasanu | G06T 7/10 |
| 2021/0082192 | A1* | 3/2021 | Guo | G06F 16/9024 |

OTHER PUBLICATIONS

FOCUSR: Feature Oriented Correspondence Using Spectral Regularization-A Method for Precise Surface Matching (Year: 2013).*

PCT International Search Report, International application No. PCT/EP2020/085394, Mar. 1, 2021.

Myronenko A. et al., "Point Set Registration: Coherent Point Drift", IEEE Transactions On Pattern Analysis and Machine Intelligence, IEEE Computer Society, USA, vol. 32, No. 12, Dec. 1, 2010 (Dec. 1, 2010), pp. 2262-2275, XP011305096.

De Goes F. et al., "A Simple and Flexible Framework to Adapt Dynamic Meshes", Computers and Graphics, Elsevier, GB, vol. 32, No. 2, Apr. 1, 2008 (Apr. 1, 2008), pp. 141-148, XP022658490.

Junyi P. et al., "Deep Mesh Reconstruction From Single RGB Images via Topology Modification Networks", 2019 IEEE/CVF International Conference On Computer Vision (ICCV), IEEE, Oct. 27, 2019 (Oct. 27, 2019), pp. 9963-9972, XP033723374.

Orasanu E. et al., "Organ-At-Risk Segmentation in Brain MRI Using Model-Based Segmentation: Benefits of Deep Learning-Based Boundary Detectors", Nov. 23, 2018 (Nov. 23, 2018), ROBOCUP 2008: ROBOCUP 2008: Robot Soccer World Cup XII; [Lecture Notes in Computer Science; Lect.Notes Computer], Springer International Publishing, Cham, pp. 291-299, XP047497946.

Zhang Z. et al., Iterative Point Matching for Registration of Free-Form Curves and Surfaces:, International Journal of Computer Vision (JCV), vol. 13, Issue 2, pp. 119-152, 1994.

Lombaert H. et al., "FOCUSR: Feature Oriented Correspondence Using Spectral Regularization—A Method for Precise Surface Matching", IEEE Transactions on Pattern Analysis and Machine Intelligence, vol. 35, No. 9, pp. 2143-2160, Sep. 2013, XP011520339.

Lombaert H. et al., "Diffeomorphic Spectral Matching of Cortical Surfaces", Information Processing and Medical Imaging (IPMI), pp. 376-389, 2013.

Shakeri M. et al., "Groupwise Shape Analysis of the Hippocampus Using Spectral Matching", Proceedings SPIE Medical Imaging, vol. 9034, Medical Imaging 2014: Image Processing; 90340W, Mar. 2014.

Orasanu E. et al., "Cortical Folding of the Preterm Brain: A Longitudinal Analysis of Extremely-Preterm Born Neonates Using Spectral Matching", Brain and Behavior, May 17, 2016;6(8):e00488.

Lombaert H. et al., "Fast Brain Matching with Spectral Correspondence", Information Processing in Medical Imaging, vol. 22, pp. 660-673, 2011.

Orasanu E.T. et al., "Longitudinal Analysis of Extreme Prematurity: A Neuroimage Investigation of Early Brain Development", Jan. 1, 2017 (Jan. 1, 2017), XP055692098. Retrieved from the Internet: URL:https://discovery.ucl.ac.uk/id/eprint/ 1551646/1/0rasanu PHD Thesis EO.pdf [retrieved on May 6, 2020] p. 34, line 22—p. 35, line 6 *.

* cited by examiner

MESH TOPOLOGY ADAPTATION

CROSS-REFERENCE TO PRIOR APPLICATIONS

This application is the U.S. National Phase application under 35 U.S.C. § 371 of International Application No. PCT/EP2020/085394, filed on Dec. 10, 2020, which claims the benefit of European Patent Application No. 19215636.2, filed on Dec. 12, 2019. These applications are hereby incorporated by reference herein.

FIELD OF THE INVENTION

This invention relates to the field of mesh topologies and more particularly to adapting a first, pre-defined mesh topology representing an organ to a second, different mesh topology of the organ.

BACKGROUND OF THE INVENTION

Annotated medical images are widely used in scientific medical research, e.g. for evaluation and training of image segmentation techniques. A popular segmentation technique is model-based segmentation (MBS). With this technique, a triangulated mesh representing an organ boundary can be adapted to a medical image in a controlled way so that the general organ shape is preserved, thus regularizing the segmentation with prior anatomical knowledge. This segmentation model has to be trained using image data and corresponding ground truth meshes of the segmented organs. Usually, these meshes are manually created by clinicians or researchers. However, this manual process is very time consuming.

The process of generating ground truth meshes may be accelerated by using an existing model developed for the same organ, the existing model having been previously trained on similar image data. Alternatively, a ground truth mesh for the organ might already be available, having been previously delineated by clinicians for a different segmentation model. For both cases, the topology of the available ground truth meshes (either from previous segmentation or a different model) might not match the existing model topology (e.g. not match in number of vertices and triangles), and, for model-based segmentation, meshes typically have to have the same topology.

One way of getting the organ meshes in the same topology is to find a correspondence between the vertices in the two different meshes, which could be provided by well-known point matching methods such as iterative closest point (ICP) or coherent point drift (CPD). However, although these methods account for global transformations in the feature space between the two shapes, one still needs to incorporate spatial regularity into the mapping, such that neighboring points in one mesh correspond to neighboring points in the other mesh.

SUMMARY OF THE INVENTION

The invention is defined by the claims.

According to examples in accordance with an aspect of the invention, there is provided a method for adapting a first, pre-defined mesh topology representing an organ to a second, different mesh topology of the organ. The method comprises: identifying correspondence between the first and second mesh topologies based on spectral matching of the first and second mesh topologies; and aligning the first, predefined mesh topology with the second mesh topology based on the identified correspondence between the first and second mesh topologies.

Proposed embodiments provide concepts for adapting a first, pre-defined mesh topology to a second, different mesh topology. For instance, embodiments may be used to adapt a first, ground truth mesh for an organ to a second, new mesh topology of the organ. In particular, embodiments may employ spectral matching to align/adapt the first, pre-defined (i.e. ground truth) mesh to a second, new mesh topology. Put another way, it is proposed to use spectral matching for aligning an already existing mesh with a new topology of the same organ. Such approaches may help to relax requirements with respect to annotated datasets.

By way of example, proposed embodiments may provide a method for using spectral matching to find the correspondence between an already existing mesh topology (e.g. obtained either from segmentation using a pre-trained model or from previous ground truth mesh generation by a user) and a newly defined mesh topology. In this way, it may be possible to define a correspondence between meshes of an organ with different topologies, because a direct vertex correspondence between the two meshes is not required due to the conversion into the spectral space. Furthermore, such a proposed approach may ensure spatial regularity, due to the use of spectral embedding (e.g. computed from the graph Laplacian of the surface meshes).

Embodiments may be based on the idea to use spectral matching for aligning an already existing mesh with a new topology of the same organ. In such embodiments, it is proposed to use spectral matching to find the correspondence between an already existing mesh topology and a newly defined mesh topology. This may enable the conversion of previously-defined ground truth meshes to a new, desired mesh topology of a model (that can then be retrained for segmentation).

By way of example, identifying correspondence between the first and second mesh topologies based on spectral matching of the first and second mesh topologies may comprise: obtaining a first spectral graph derived from the first mesh topology; obtaining a second spectral graph derived from the second mesh topology; decomposing the first and second spectral graphs to determine spectral coordinates from the first and second spectral graphs; analyzing the determined spectral coordinates to identify matches between the first and second spectral graphs; and identifying correspondence between the first and second mesh topologies based on the identified matches. Embodiments may therefore employ conventional/known spectral graph generation and/or matching processes, thus leveraging widely known and/or available processes.

In some embodiments, aligning the first, predefined mesh topology with the second mesh topology may comprise aligning spectral components of the first and second mesh topologies. For instance, aligning spectral components may comprise processing the first mesh topology with a point transformation method on both meshes, such as a Coherent Point Drift (CPD) method or an Iterative Closest Point (ICP) method for example. Known point matching methods may therefore be employed, thus reducing the complexity and/or cost of embodiments for example.

In an exemplary embodiment, aligning the first, predefined mesh topology with the second mesh topology may comprise resampling the first mesh topology based on the identified correspondence between the first and second mesh topologies.

Because the proposed concepts may enable the conversion of previously-defined ground truth meshes to a new, desired mesh topology of a model (that can then be retrained for segmentation), it will be understood that embodiments of the invention may be leveraged for use in image segmentation. Thus, according to another aspect of the invention, there is provided a method for segmentation of a medical image of an organ, the method comprising: adapting a first mesh topology representing the organ to a second, different mesh topology of the organ according to a proposed embodiment; and performing model-based segmentation of the image using the adapted first mesh topology.

According to another aspect, there is provided a computer program product for adapting a first, pre-defined mesh topology representing an organ to a second, different mesh topology of the organ, wherein the computer program product comprises a computer-readable storage medium having computer-readable program code embodied therewith, the computer-readable program code configured to perform all of the steps of a proposed embodiment.

Thus, there may also be provided a computer system comprising: a computer program product according to proposed embodiment; and one or more processors adapted to perform a method according to a proposed concept by execution of the computer-readable program code of said computer program product.

According to still another aspect of the invention, there is provided a system for adapting a first, pre-defined mesh topology representing an organ to a second, different mesh topology of the organ, the system comprising: an analysis component configured to identify correspondence between the first and second mesh topologies based on spectral matching of the first and second mesh topologies; and a mesh alignment component configured to align the first, predefined mesh topology with the second mesh topology based on the identified correspondence between the first and second mesh topologies.

The system may be remotely located from a user device for adapting a first mesh topology to a second, different mesh topology. In this way, a user (such as a medical professional) may have an appropriately arranged system that can receive information at a location remotely located from the system for adapting a first, mesh topology to a second, different mesh topology. Embodiments may therefore enable a user to adapt a first mesh topology to a second, different mesh topology using a local system (which may, for example, comprise a portable display device, such as a laptop, tablet computer, mobile phone, PDA, etc.). By way of example, embodiments may provide an application for a mobile computing device, and the application may be executed and/or controlled by a user of the mobile computing device.

The system may further include: a server device comprising the system for adapting a first mesh topology to a second, different mesh topology; and a client device comprising a user-interface. Dedicated data processing means may therefore be employed for the purpose of adapting a first mesh topology to a second, different mesh topology, thus reducing processing requirements or capabilities of other components or devices of the system.

The system may further include a client device, wherein the client device comprises the mesh alignment component and a display unit. In other words, a user (such as a doctor or medical professional) may have an appropriately arranged client device (such as a laptop, tablet computer, mobile phone, PDA, etc.) which processes received data in order to adapt a first mesh topology to a second, different mesh topology and generate a display control signal. Purely by way of example, embodiments may therefore provide a mesh-based annotation system that enables medical analysis of one or more subjects (e.g. patients) from a single, remote location, wherein communication between a subject and monitoring user (e.g. nurse or doctor) is provided and can have its functionality extended or modified according to proposed concepts, for example.

It will be understood that processing capabilities may therefore be distributed throughout the system in different ways according to predetermined constraints and/or availability of processing resources.

These and other aspects of the invention will be apparent from and elucidated with reference to the embodiment(s) described hereinafter.

BRIEF DESCRIPTION OF THE DRAWINGS

For a better understanding of the invention, and to show more clearly how it may be carried into effect, reference will now be made, by way of example only, to the accompanying drawings, in which.

DETAILED DESCRIPTION OF THE EMBODIMENTS

Figure 1:
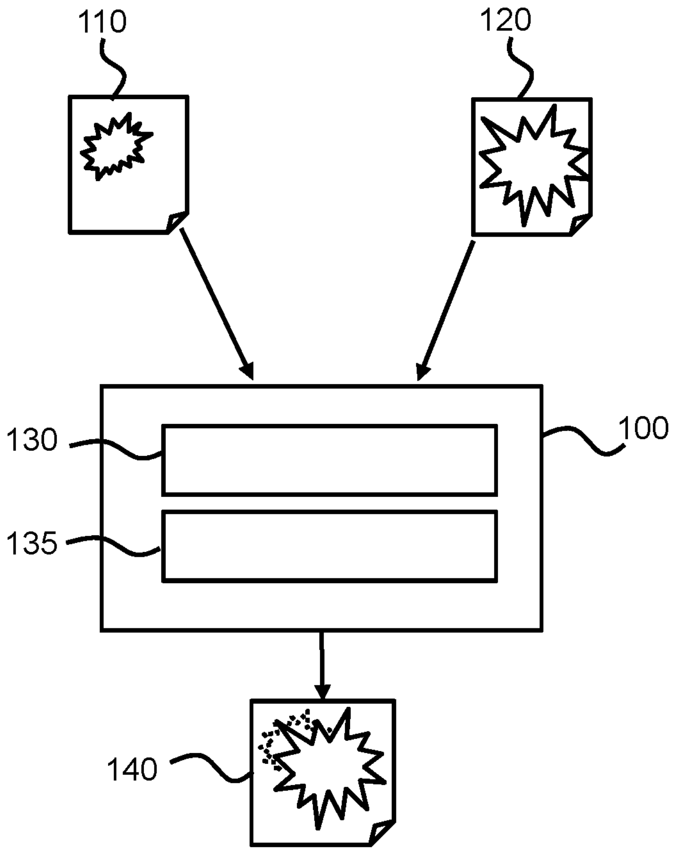
FIG. 1 is a simplified block diagram of a proposed embodiment of a system for adapting a first, pre-defined mesh topology representing an organ to a second, different mesh topology of the organ.

The invention will be described with reference to the Figs.

It should be understood that the detailed description and specific examples, while indicating exemplary embodiments of the apparatus, systems and methods, are intended for purposes of illustration only and are not intended to limit the scope of the invention. These and other features, aspects, and advantages of the apparatus, systems and methods of the present invention will become better understood from the following description, appended claims, and accompanying drawings. The mere fact that certain measures are recited in mutually different dependent claims does not indicate that a combination of these measures cannot be used to advantage.

Variations to the disclosed embodiments can be understood and effected by those skilled in the art in practicing the claimed invention, from a study of the drawings, the disclosure and the appended claims. In the claims, the word "comprising" does not exclude other elements or steps, and the indefinite article "a" or "an" does not exclude a plurality.

It should be understood that the Figs. are merely schematic and are not drawn to scale. It should also be understood that the same reference numerals are used throughout the Figs. to indicate the same or similar parts.

Proposed is an approach for enabling the adaptation of a first, pre-defined mesh topology representing an organ to a second, different mesh topology of the organ. Embodiments may thus be used for translating a mesh from a first, defined (e.g. ground truth with annotations) model space to another. This may enable the ground truth annotations of the first model space to be used to train a new, different model (e.g. that is designed to take a new problem).

Embodiments propose to use spectral matching to find the correspondence between a first, pre-defined (e.g. pre-existing) mesh topology of an organ (either obtained from segmentation of the organ using a pre-trained model or from previous ground truth mesh generation by a clinician) and second (e.g. newly defined) mesh topology. This may therefore enable conversion of a pre-defined ground truth mesh to a new mesh topology of a model that can then be re-trained for segmentation.

Spectral matching is widely known and therefore detailed description of spectral matching is omitted from this description. However, by way of brief explanation, the spectral decomposition of the graph Laplacian associated with complex shapes provides eigenfunctions (modes) which are invariant to isometries. Each vertex on the shape could be uniquely represented with a combinations of the eigenmodal values at each point, sometimes called spectral coordinates. Spectral matching consists of establishing the point correspondences by pairing vertices on different shapes that have the most similar spectral coordinates. Spectral graph theory thus offers a solution for matching surface meshes with different topologies in the spectral domain, and may therefore provide applications for matching different meshes to create atlases.

The inventors propose to leverage spectral matching in order to bring a previously defined mesh into a new model topology. In this way, proposed embodiments may enable the identification of correspondence between meshes of the same organs but with different topologies (e.g. brains, hearts, kidneys, livers or lungs of two different subjects/patients). In particular, due to conversion into the spectral space, a direct vertex correspondence between meshes need not be required. Furthermore, such an approach may ensure spatial regularity, due to the use of the spectral embedding computed from the graph Laplacian of the surface meshes for example.

Proposed embodiments may therefore be employed for segmentation of a medical image of an organ. Such a method may include: adapting a first mesh topology representing the organ to a second, different mesh topology of the organ according to a proposed embodiment. Model-based segmentation of the image may then be performed using the adapted first mesh topology. Semi-automatic ground truth segmentations may therefore be facilitated by the proposed concept(s). By employing previously developed models, the process may be accelerated (because a user may only need to implement small corrections, rather than manually creating a new mesh for example). Furthermore, multi-purpose data may be provided, and this may, for instance, be used for more projects where the same organ needs to be delineated but with different topology.

By way of example only, illustrative embodiments may be utilized in many different types of clinical, medical or subject-related environments, such as a hospital, doctor's office, medical-research facility, ward, care home, person's home, etc.

To aid understanding of the proposed concept(s), an exemplary embodiment of a system for adapting a first, pre-defined mesh topology representing an organ to a second, different mesh topology of the organ will now be described with reference to FIG. 1.

FIG. 1 is a simplified block diagram of a proposed embodiment. A system 100 according to a proposed is configured to obtain (e.g. receive via an input interface) a first, pre-defined mesh topology 110 representing an organ (such as a liver of a first subject, for example). The system 100 is also adapted to obtain (e.g. receive via an input interface) a second, different mesh topology 120 of the organ (such as a liver of a second subject, for example). The system is configured to adapt the first, pre-defined mesh topology 110 to the second mesh topology 120. Put another way, the system 100 is configured tor translating a mesh from a first, defined (e.g. ground truth with annotations) model space to another. This may enable the ground truth annotations of the first model space to be used to train a new, different model.

More specifically, the system 100 comprises an analysis component 130 that is configured to undertake spectral matching of the first 110 and second 120 mesh topologies to identify correspondence between the first 110 and second 120 mesh topologies. A mesh alignment component 135 of the system is then configured to align the first, predefined mesh topology 110 with the second mesh topology 120 based on the correspondence between the first and second mesh topologies (as identified by the analysis component 130).

The aligned mesh topology 140 is output from the system 100 (e.g. via an output interface), the aligned mesh topology 140 being adapted to the second mesh topology 120. In this way, annotations of the first mesh topology 110 are carried through into the aligned mesh topology 140, but are also aligned with the second mesh topology.

By way of further illustration and description, an exemplary method according to an embodiment will now be described with reference to FIG. 2.

Figure 2:
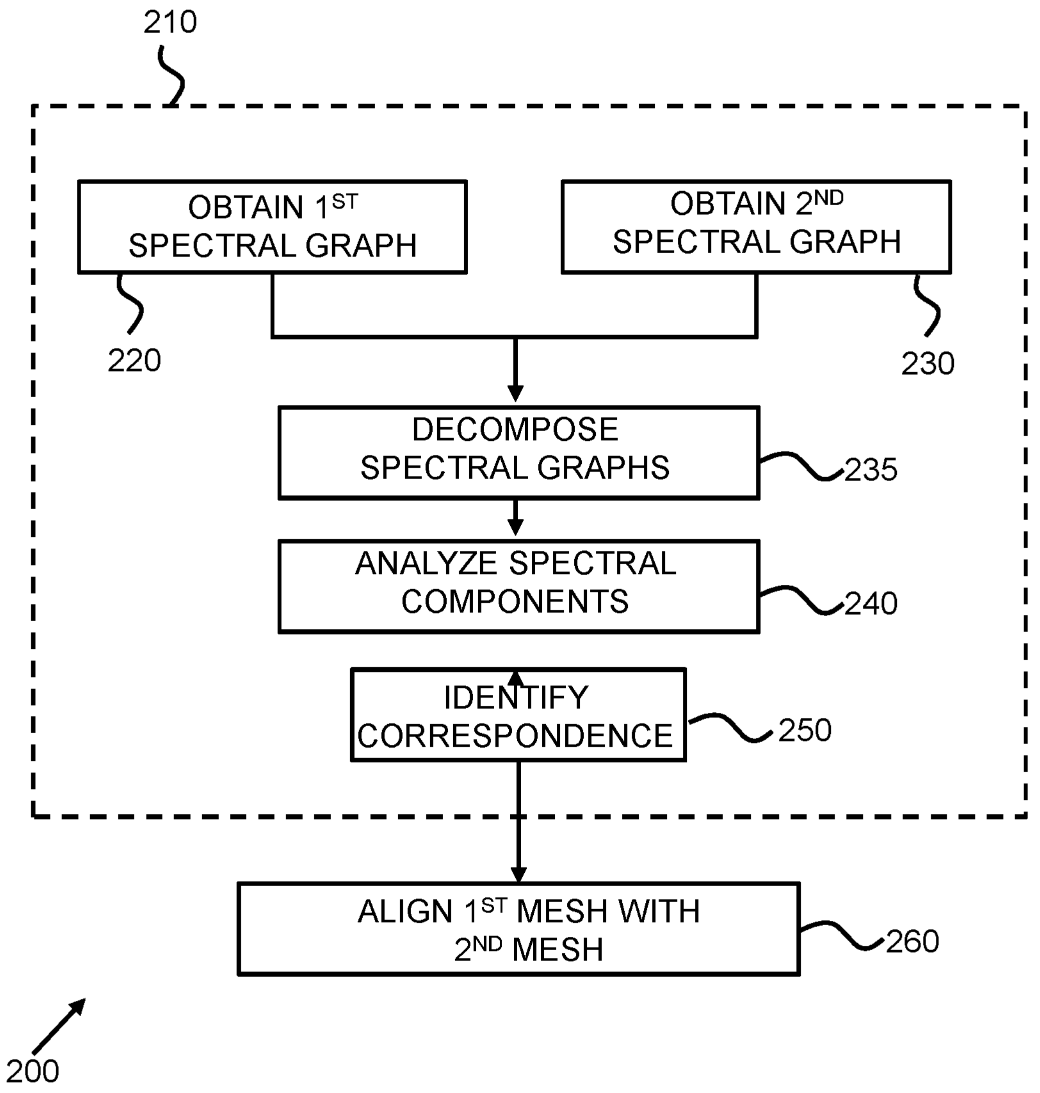
FIG. 2 is a simplified flow diagram of a proposed embodiment of a method for adapting a first, pre-defined mesh topology representing an organ to a second, different mesh topology of the organ.

FIG. 2 is a simplified flow diagram of a proposed embodiment of a method 200 for adapting a first, pre-defined mesh topology representing an organ to a second, different mesh topology of the organ. The method 200 comprises first step 210 of identifying correspondence between the first and second mesh topologies based on spectral matching of the first and second mesh topologies. In more detail, the step 210 of identifying correspondence between the first and second mesh topologies based on spectral matching of the first and second mesh topologies comprises: obtaining 220 a first spectral graph derived from the first mesh topology; and 230 obtaining a second spectral graph derived from the second mesh topology. Here it is noted that the first and second spectral graphs may be obtained in any order. Also, obtaining the spectral graphs may comprise generating the spectral graphs or, alternatively, simply receiving generated spectral graphs from an external component. After having obtained the first and second spectral graphs, the step 210 of identifying correspondence between the first and second mesh topologies then also includes the step 235 of decomposing the first and second spectral graphs to determine the spectral coordinates. The spectral coordinates are then analyzed in step 240 to identify matches between the first and second spectral graphs. Based on the identified matches, correspondence between the first and second mesh topologies is then identified in step 250.

The method 200 then comprises second step 260 of aligning the first, predefined mesh topology with the second mesh topology based on the identified correspondence between the first and second mesh topologies. Here, the step 260 of aligning the first, predefined mesh topology with the second mesh topology comprises aligning spectral components of the first and second mesh topologies. More specifically, in this exemplary embodiment, aligning spectral components comprises processing the first mesh topology with a point transformation method, such as a Coherent Point Drift method or an Iterative Closest Point (ICP) method for example. Alternatively, or additionally, aligning the first, predefined mesh topology with the second mesh topology may comprise resampling the first mesh topology based on the identified correspondence between the first and second mesh topologies.

From the above-described exemplary embodiments, it will be appreciated there proposed concepts may facilitate the generation of consistent mesh-based annotations for images using spectral matching. In particular, proposed embodiments employ spectral matching to find the correspondence between an already existing mesh topology and a newly defined mesh topology. Instead of direct vertex correspondence, it is proposed to use spectral embeddings computed from graph Laplacian of the surface meshes.

Thus, there is proposed a method for using spectral matching to find the correspondence between an already existing mesh topology (either obtained from segmentation of the organ using a pre-trained model or from previous ground truth mesh generation by a clinician) and a newly defined mesh topology. This may be achieved by using the spectral embeddings of the two shapes, calculated independently, and looking for a match between a defined mesh (i.e. ground truth) and a template (i.e. the new mesh topology). After a match has been defined, the ground truth mesh may then be resampled in the new topology. This is supported by the spectral matching which offers a point-to-point mesh correspondence.

Figure 3:
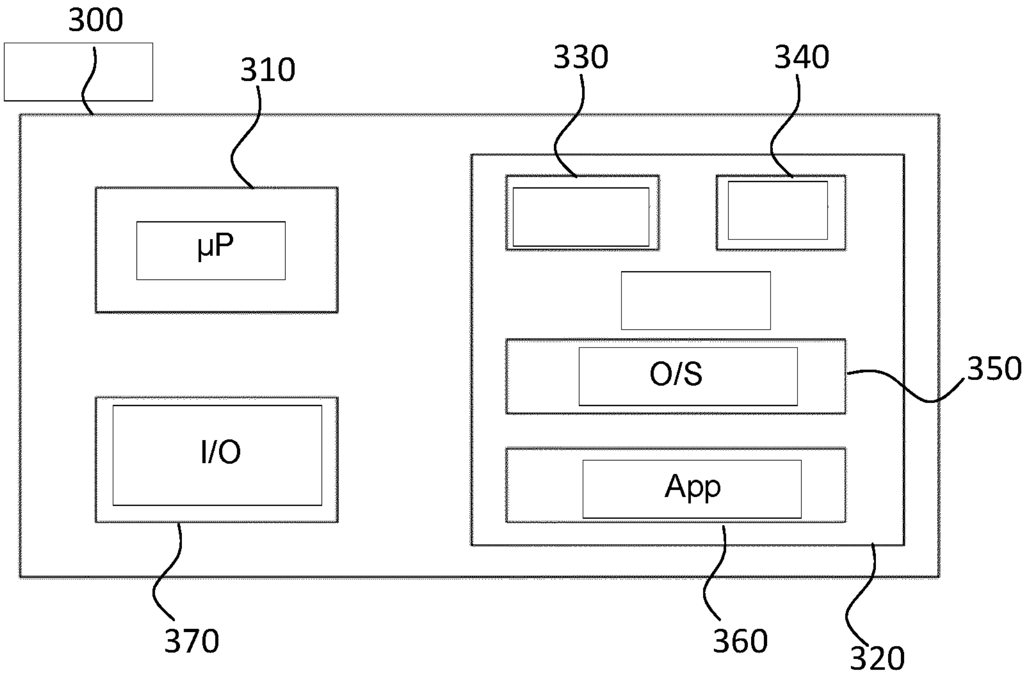
FIG. 3 is a simplified block diagram of a computer within which one or more parts of an embodiment may be employed.

FIG. 3 illustrates an example of a computer 300 within which one or more parts of an embodiment may be employed. Various operations discussed above may utilize the capabilities of the computer 300. For example, one or more parts of a system for providing a subject-specific user interface may be incorporated in any element, module, application, and/or component discussed herein. In this regard, it is to be understood that system functional blocks can run on a single computer or may be distributed over several computers and locations (e.g. connected via internet).

The computer 300 includes, but is not limited to, PCs, workstations, laptops, PDAs, palm devices, servers, storages, and the like. Generally, in terms of hardware architecture, the computer 300 may include one or more processors 310, memory 320, and one or more I/O devices 370 that are communicatively coupled via a local interface (not shown). The local interface can be, for example but not limited to, one or more buses or other wired or wireless connections, as is known in the art. The local interface may have additional elements, such as controllers, buffers (caches), drivers, repeaters, and receivers, to enable communications. Further, the local interface may include address, control, and/or data connections to enable appropriate communications among the aforementioned components.

The processor 310 is a hardware device for executing software that can be stored in the memory 320. The processor 310 can be virtually any custom made or commercially available processor, a central processing unit (CPU), a digital signal processor (DSP), or an auxiliary processor among several processors associated with the computer 300, and the processor 310 may be a semiconductor based microprocessor (in the form of a microchip) or a microprocessor.

The memory 320 can include any one or combination of volatile memory elements (e.g., random access memory (RAM), such as dynamic random access memory (DRAM), static random access memory (SRAM), etc.) and nonvolatile memory elements (e.g., ROM, erasable programmable read only memory (EPROM), electronically erasable programmable read only memory (EEPROM), programmable read only memory (PROM), tape, compact disc read only memory (CD-ROM), disk, diskette, cartridge, cassette or the like, etc.). Moreover, the memory 320 may incorporate electronic, magnetic, optical, and/or other types of storage media. Note that the memory 320 can have a distributed architecture, where various components are situated remote from one another, but can be accessed by the processor 310.

The software in the memory 320 may include one or more separate programs, each of which comprises an ordered listing of executable instructions for implementing logical functions. The software in the memory 320 includes a suitable operating system (O/S) 350, compiler 340, source code 330, and one or more applications 360 in accordance with exemplary embodiments. As illustrated, the application 360 comprises numerous functional components for implementing the features and operations of the exemplary embodiments. The application 360 of the computer 300 may represent various applications, computational units, logic, functional units, processes, operations, virtual entities, and/or modules in accordance with exemplary embodiments, but the application 360 is not meant to be a limitation.

The operating system 350 controls the execution of other computer programs, and provides scheduling, input-output control, file and data management, memory management, and communication control and related services. It is contemplated by the inventors that the application 360 for implementing exemplary embodiments may be applicable on all commercially available operating systems.

Application 360 may be a source program, executable program (object code), script, or any other entity comprising a set of instructions to be performed. When a source program, then the program is usually translated via a compiler (such as the compiler 340), assembler, interpreter, or the like, which may or may not be included within the memory 320, so as to operate properly in connection with the O/S 350. Furthermore, the application 360 can be written as an object oriented programming language, which has classes of data and methods, or a procedure programming language, which has routines, subroutines, and/or functions, for example but not limited to, C, C++, C#, Pascal, BASIC, API calls, HTML, XHTML, XML, ASP scripts, JavaScript, FORTRAN, COBOL, Perl, Java, ADA, .NET, and the like.

The I/O devices 370 may include input devices such as, for example but not limited to, a mouse, keyboard, scanner, microphone, camera, etc. Furthermore, the I/O devices 370 may also include output devices, for example but not limited to a printer, display, etc. Finally, the I/O devices 370 may further include devices that communicate both inputs and outputs, for instance but not limited to, a NIC or modulator/demodulator (for accessing remote devices, other files, devices, systems, or a network), a radio frequency (RF) or other transceiver, a telephonic interface, a bridge, a router, etc. The I/O devices 370 also include components for communicating over various networks, such as the Internet or intranet.

If the computer 300 is a PC, workstation, intelligent device or the like, the software in the memory 320 may further include a basic input output system (BIOS) (omitted for simplicity). The BIOS is a set of essential software routines that initialize and test hardware at startup, start the 0/S 350, and support the transfer of data among the hardware devices. The BIOS is stored in some type of read-only-memory, such as ROM, PROM, EPROM, EEPROM or the like, so that the BIOS can be executed when the computer 300 is activated.

When the computer 300 is in operation, the processor 310 is configured to execute software stored within the memory 320, to communicate data to and from the memory 320, and to generally control operations of the computer 300 pursuant to the software. The application 360 and the 0/S 350 are read, in whole or in part, by the processor 310, perhaps buffered within the processor 310, and then executed.

When the application 360 is implemented in software it should be noted that the application 360 can be stored on virtually any computer readable medium for use by or in connection with any computer related system or method. In the context of this document, a computer readable medium may be an electronic, magnetic, optical, or other physical device or means that can contain or store a computer program for use by or in connection with a computer related system or method.

The application 360 can be embodied in any computer-readable medium for use by or in connection with an instruction execution system, apparatus, or device, such as a computer-based system, processor-containing system, or other system that can fetch the instructions from the instruction execution system, apparatus, or device and execute the instructions. In the context of this document, a "computer-readable medium" can be any means that can store, communicate, propagate, or transport the program for use by or in connection with the instruction execution system, apparatus, or device. The computer readable medium can be, for example but not limited to, an electronic, magnetic, optical, electromagnetic, infrared, or semiconductor system, apparatus, device, or propagation medium.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

A single processor or other unit may fulfill the functions of several items recited in the claims.

A computer program may be stored/distributed on a suitable medium, such as an optical storage medium or a solid-state medium supplied together with or as part of other hardware, but may also be distributed in other forms, such as via the Internet or other wired or wireless telecommunication systems.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figs. illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the Figs.. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The invention claimed is:

1. A method for aligning first, pre-defined mesh topology representing an organ to a second, different mesh topology of the organ, the method comprising:

identifying correspondence between the first and second mesh topologies based on spectral matching of the first and second mesh topologies;

aligning the first, predefined mesh topology with the second mesh topology based on the identified correspondence between the first and second mesh topologies, wherein the aligning comprises transforming shape of the first mesh topology based on the spectral matching of the first and second mesh topologies; and resampling the first mesh topology in the second mesh topology based on the identified correspondence between the first and second mesh topologies.

2. The method of claim 1, wherein identifying correspondence between the first and second mesh topologies based on spectral matching of the first and second mesh topologies comprises:

obtaining a first spectral graph derived from the first mesh topology;

obtaining a second spectral graph derived from the second mesh topology; decomposing the first and second spectral graphs to determine spectral coordinates from the first and second spectral graphs;

analyzing the determined spectral coordinates to identify matches between the first and second spectral graphs; and identifying correspondence between the first and second mesh topologies based on the identified matches.

3. The method of claim 1, wherein aligning the first, predefined mesh topology with the second mesh topology comprises:

aligning spectral components of the first and second mesh topologies.

4. The method of claim 3, wherein transforming the shape of the first mesh topology based on the spectral matching of the first and second mesh topologies comprises processing the first mesh topology with a point transformation method.

5. The method of claim 4, wherein the point transformation method comprises a Coherent Point Drift method.

6. The method of claim 1, further comprising:

performing model-based segmentation of the image using the aligned first mesh topology.

7. A system for aligning a first, pre-defined mesh topology representing an organ to a second, different mesh topology of the organ, the system comprising:

a processor configured to:

identify correspondence between the first and second mesh topologies based on spectral matching of the first and second mesh topologies;

align the first, predefined mesh topology with the second mesh topology based on the identified correspondence between the first and second mesh topologies, wherein aligning the first mesh topology comprises transforming shape of the first mesh topology based on the spectral matching of the first and second mesh topologies; and resample the first mesh topology in the second mesh topology based on the identified correspondence between the first and second mesh topologies.

8. The system of claim 7, wherein the processor is further configured to:

obtain a first spectral graph derived from the first mesh topology and to obtain a second spectral graph derived from the second mesh topology;

decompose the first and second spectral graphs to determine spectral components and to identify matches between the first and second spectral graphs based on the determined spectral components; and identify correspondence between the first and second mesh topologies based on the identified matches.

9. The system of claim 7, wherein the processor is further configured to align spectral components of the first and second mesh topologies.

10. The system of claim 9, wherein, to transform the shape of the first mesh topology based on the spectral matching of the first and second mesh topologies, the processor is further configured to process the first mesh topology with a point transformation method.

11. The system of claim 10, wherein the point transformation method comprises a Coherent Point Drift method.

12. The system of claim 7 wherein the processor is further configured to:

perform model-based segmentation of the image using the aligned first mesh topology.

13. The method according to claim 1, wherein aligning the first, predefined mesh topology with the second mesh topology includes aligning structural features of the first, predefined mesh topology and the second mesh topology.

14. The method according to claim 13, wherein aligning structural features of the first, predefined mesh topology and the second mesh topology includes pairing vertices of the first, predefined mesh topology and the second mesh topology.

15. A non-transitory computer readable medium comprising computer-readable executable instructions, which when executed by a processor, cause the processor to:

identify correspondence between the first and second mesh topologies based on spectral matching of the first and second mesh topologies;

align the first, predefined mesh topology with the second mesh topology based on the identified correspondence between the first and second mesh topologies, wherein the aligning of the first mesh topology comprises transforming shape of the first mesh topology based on the spectral matching of the first and second mesh topologies; and resample the first mesh topology in the second mesh topology based on the identified correspondence between the first and second mesh topologies.

16. The non-transitory computer readable medium of claim 15, wherein the first mesh topology is a ground truth mesh topology with ground truth annotations of a first model space translated to a second model space.

17. The non-transitory computer readable medium of claim 16, wherein the ground truth annotations are carried into the aligned mesh topology.

18. The non-transitory computer readable medium of claim 15, wherein the first mesh topology is a ground truth mesh topology that is converted to a new mesh topology of a model that is re-trained for segmentation.

* * * * *